United States Patent [19]

Mears

[11] 4,108,916

[45] Aug. 22, 1978

[54] PURIFICATION OF SATURATED HYDROCARBONS

[75] Inventor: Whitney Harris Mears, Pittsfield, Mass.

[73] Assignee: Allied Chemical Corporation, Morris Township, Morris County, N.J.

[21] Appl. No.: 740,152

[22] Filed: Nov. 8, 1976

[51] Int. Cl.² .............................................. C07C 9/02
[52] U.S. Cl. ............................... 260/676 R; 208/273
[58] Field of Search ..................... 260/676 R; 208/273

[56] References Cited

U.S. PATENT DOCUMENTS

| | | | |
|---|---|---|---|
| 3,168,585 | 2/1965 | McCarthy | 260/677 |
| 3,254,135 | 5/1966 | McCarthy et al. | 260/677 |
| 3,300,539 | 1/1967 | Sherk | 260/677 |
| 3,370,003 | 2/1968 | Borst | 208/351 |
| 3,591,654 | 7/1971 | Newton | 260/683.61 |
| 3,979,474 | 9/1976 | Zerrwick | 260/677 |

OTHER PUBLICATIONS

Polgar et al., Organic Analysis, vol. 3, pp. 294–298.
Gehlawat et al., Chem. Eng. Science, 1968, vol. 23, pp. 1173–1180.
Kalichevsky et al., Petroleum Refining with Chemicals, Elsevier Pub. Co., New York, 1956, pp. 72–87.

*Primary Examiner*—C. Davis
*Attorney, Agent, or Firm*—Alan M. Doernberg; Jay P. Friedenson

[57] ABSTRACT

Aerosol propellants from the class n-butane, isobutane and propane cause increased amounts of corrosion with greater than 5 parts per million unsaturates as impurities. Unsaturate levels are reduced below 5 parts per million, and preferably below 2 parts per million and most preferably below 1 part per million, by passing the saturated hydrocarbon containing unsaturated contaminants through a sulfuric acid scrubber for a length of time sufficient to remove unsaturated contaminants in excess of 5 parts per million and passing the outflow from the sulfuric acid scrubber through a basic demister to remove the sulfuric acid. The sulfuric acid scrubbing takes place in a column by liquid-liquid contact. The saturated hydrocarbon is then allowed to vaporize, and is passed successively through a basic demister and, if moist, a drying agent.

18 Claims, No Drawings

PURIFICATION OF SATURATED HYDROCARBONS

BACKGROUND OF THE INVENTION

Lower saturated hydrocarbons have been used in large quantities as propellants in aerosol cans. In particular, isobutane, n-butane and propane have been used either alone or in +with halogenated hydrocarbons and especially fluorocarbons or chlorofluorocarbons.

Unexplainably, certain sources of hydrocarbon, and especially isobutane, have proved satisfactory for aerosol use and have been designated aerosol grade hydrocarbons. Most sources of hydrocarbons, and especially isobutane, have not been successfully used in aerosol containers without unacceptable levels of corrosion and odor.

Limited sources of hydrocarbons, and particularly isobutane, have been found to be satisfactory for use as propellants in aerosols. In particular, most sources of "technical" grade isobutane cause unsatifactory levels of corrosion and odor when placed in aerosol cans and allowed to remain there for several weeks or months. Examination of "technical grade" isobutane by conventional techniques has not determined the nature of the contaminant that causes such corrosion and odor. In particular, molecular sieves through which "technical grade" isobutane is passed do not indicate an impurity in "technical grade" isobutane not found in "aerosol grade" isobutane. Similarly, tests for sulfur compounds by mass spectroscopy revealed no evidence of sulfur compounds at the 50 part per billion level. Furthermore, no resolution between isobutane and isobutene was possible using mass spectroscopy.

Fractionation in a Podbelniak type column did not raise the impurities to a level in which the impurity could be detected. The only detected impurity, 2-ethylhexene-1, was found in trace amounts.

BRIEF DESCRIPTION OF THE INVENTION

The invention includes purifying a saturated hydrocarbon selected from the group consisting of n-butane, isobutane and propane with less than 5 parts per million, and preferably less than 2 parts per million and most preferably less than 1 parts per million, of unsaturated contaminants by passing the unsaturated hydrocarbon containing unsaturated contaminants through a sulfuric acid scrubber for a length of time sufficient to remove unsaturated contaminants in excess of about 1, 2 or 5 parts per million and passing the outflow through a basic demister to remove sulfuric acid mist from the saturated hydrocarbon. In some preferred embodiments, the outflow from the demister is passed through a drying agent.

In preferred embodiments, the saturated hydrocarbon containing unsaturated contaminants is liquified and passed in liquid form through a column containing sulfuric acid, thus promoting a maximum of liquid—liquid contact to remove the unsaturates. The hydrocarbon is then allowed to gassify after which it is passed through a column containing a demister. In some preferred embodiments, a basic aqueous solution is used as a demister and the hydrocarbon gas is bubbled through the aqueous solution. In other embodiments, a basic solid particle, such as alumina, is used to demist the saturated hydrocarbon.

Preferred sulfuric acid scrubbers include concentrated sulfuric acid, such as 96% sulfuric acid, and concentrated sulfuric acid combined with up to 20% $P_2O_5$, and preferably 15% $P_2O_5$. Other sulfuric acid scrubbers include a concentrated sulfuric acid combined with cupric sulfate or mercuric sulfate catalyst.

DETAILED DESCRIPTION OF THE INVENTION

It has been surprisingly found that small quantities of unsaturates, and particularly unsaturated butenes, in conventional sources of technical isobutane cause the high corrosion and odor formation that makes these sources objectionable for aerosol use. Sulfuric acid absorption is known generically as a technique for removing unsaturates from saturated hydrocarbons, A. Polgar and J. L. Jungnickel, *Organic Analysis*, Vol. 3, pages 294–298; *Brennstoff*, Vol. 8, page 353 (1927).

Having appreciated the desirability of low unsaturate levels for aerosol use, the present invention has made use of a known type of system, a sulfuric acid scrubber and a basic demister. The invention is not, however, limited to the sulfuric acid and basic columns used in the following examples, but includes the use of concentrated sulfuric acid with up to about 20 percent $P_2O_5$, and preferably between about 10 and about 15 percent $P_2O_5$. The sulfuric acid bath may also contain a sulfonation catalyst in catalytic amounts such as $HgSO_4$ or $CuSO_4$, although it has been discovered that these catalysts are not required to obtain unsaturate levels below about 1 part per million.

Similarly, the basic column need not be an aqueous solution of sodium hydroxide, but could be an aqueous solution of any basic hydroxide, oxide or salt. For example, up to saturated solutions of alkali or alkalai earth hydroxides could be used, as for example LiOH, NaOH, KOH, $Ca(OH)_2$, $Ba(OH)_2$. In addition, solid demisters may be used, as for example alumina particles or many other basic solid oxides and salts. The broad range of demisters to remove sulfuric acid from a vapor are well known in the art.

Use of a drying column downstream from the demister column is necessary only where the outflow from the demister column contains significant amounts of moisture. With solid particles such as alumina particles as the demister, the drying column can usually be dispensed with. The wide variety of drying columns, using dessicants such as calcium sulfate or calcium chloride, are well known in the art.

It should be appreciated that in the sulfuric acid column, unsaturates react to form sulfate esters as by the reaction $(CH_3)_2C=CH_2 + H_2SO_4 \rightarrow (CH_3)_2CH-CH_2-SO_3H$. The ester remains in the sulfuric acid phase while the saturated hydrocarbons remain unreacted and in a separate phase. Saturates may then gasify at the end of the column free of unsaturate impurities.

The length of time to which a saturated hydrocarbon sample is exposed to sulfuric acid will control the extent of unsaturate removal. The unsaturate level can be continually monitored by taking samples and evaluating by the column techniques of Example 1. The extent of unsaturate removal can be increased, if insufficient, by increasing the length of the sulfuric acid column, by decreasing the hydrocarbon flow rate, increasing the contact surface area or by passing the hydrocarbon through the column more than once.

The conditions required for unsaturate removal down to below 5, and preferably below 2 and most preferably below 1 ppm depend to a large extent upon column size and the degree of liquid-liquid contact. Raschig rings were found in the Examples below to provide sufficient liquid-liquid contact for purification below 1 ppm unsaturates to be achieved. Longer columns or slower throughput could be used to improve the purification if the analysis technique described in Example 1 detects unsaturates above desired levels.

By concentrated sulfuric acid is meant more than about 80% sulfuric acid, and preferably more than 90% sulfuric acid and most preferably commercially available technical grade sulfuric acid which is about 96%. The actual concentration of sulfuric acid in the column may be lower because of $P_2O_5$ or catalyst amounts.

EXAMPLE I

Impurity Detection

Analysis by use of a gas chromatography technique in which ethylene glycol and silver nitrate are introduced successfully revealed an unsaturated impurity at between 1 and 50 parts per million in "technical grade" isobutane not present in "aerosol grade" isobutane. In particular, a 15 ft. by ⅛ inch inside diameter stainless steel column, packed with a mixture of 70 percent Chromosorb P (a support made by the Johns Manville Company from Sil-O-Cel C-22 firebrick), (60–80 mesh), 25 percent ethylene glycol and 5 percent silver nitrate, by weight, was used in which the silver nitrate and ethylene glycol were dissolved in methanol and mixed with the Chromosorb P. The methanol was wetted off at room temperature and the packing dried over night in a vacuum oven at room temperature. Using helium as a carrier gas flowing at about 60 ml/min, hydrocarbon was detected in the outflow port using a flame ion detector.

Using this technique, impurity peaks were measurable, and were estimated using area normalization, under 50 parts per million, and down to about 1 part per million.

An alternative procedure has been tested following the directions for a Perkins-Elmer Model 900 chromatograph. A six foot by one-half inch stainless steel column was peaked with phenylisocyanate chemically bonded on Poracil C (the bonded product is available from Waters Associates, Inc. of Milford, Mass. and is sold as DURAPAK Phenylisocyanate/Porasil C 80/100). Nitrogen at 5 milliliters per minute is passed through the column carrying 0.5 ml of sample injected into the chromatograph. Peaks were measured with the flame-ionization detector sold with the Perkins-Elmer Model 900 chromatograph. Using this device, normalized area calculations of the results when standard samples were run, established a consistently accurate reading within about 1 PPM below about 10 PPM, and detected peaks at about 0.5 PPM of isobutylene. An expected error of about 5% was achieved.

EXAMPLES 2-7

Purification

Conventional "technical grade" isobutane was purified using a sulfuric acid column. The isobutane was liquified and passed upward through a sulfuric acid tower using a 30 inch long, 1½ inch diameter glass pipe packed with Raschig rings. The rings gave good results since they promoted good isobutane-reagent contact.

Some isobutane decomposition by the sulfuric acid scrubbing liquid was observed, but did not proceed at unsatisfactory levels.

The outflow from the sulfuric acid column was allowed to gasify under decreased pressure and increased temperature until a stream of isobutane vapor containing sulfuric acid mist was detected. The vapor was then passed vertically upward through a sodium hydroxide tower, also a 30 inch long, 1½ inch diameter glass pipe, containing 5 percent sodium hydroxide in water. The outflow from this tower was free of sulfate in excess of one part per million, and generally in excess of 50 parts per billion, but contained some moisture. The moisture was removed by passing the outflow through a dryer, using a third 30 inch by 1½ inch diameter glass pipe, containing a desiccant such as $CaSO_4$. The outflow was analyzed using the system of Example 1.

Because the amount of unsaturates absorbed by the sulfuric acid is quite low for the relative volumes of sulfuric acid used, the sulfuric acid column need not be regenerated until after large quantities of isobutane have been purified. Furthermore, since no boiling point is reported for the n-butyl sulfuric acid monoester, it appears that it decomposes on heating. Accordingly, the n-butyl sulfuric acid monoester can be removed from the sulfuric acid by heating of the liquid to regenerate the acid.

Examples of runs using this process are contained in Tables 1 and 2. In each case, the isobutane sample was passed at about 3 atmospheres pressure as a liquid through the sulfuric acid column, gasified, and then passed through 5% NaOH in water. The product was dried through a $CaSO_4$ column. After a portion of the product was condensed at −80° C, two samples were obtained as shown in the "liquid phase" and "vaporized" columns of Table I.

TABLE 1

PROCESS RUNS - ISOBUTANE PURIFICATION*
T = Ambient Room Temp. 25° C., P = Isobutane Vapor Pressure, 66 psia at 88° C.

| Example | Isobutane Input Analysis | Throughput gms/minute | Scrubbing Liquid | Isobutane Output Liquid Phase | Vaporized |
|---|---|---|---|---|---|
| 2 | Sample Wgt. +Toca Off Sieves++ 36 ppm unsat. 1800 gms. | 70 | 96% $H_2SO_4$ + 15% $P_2O_4$ | <1 ppm unsat. <0.01 ppm $SO_4$ | <1 ppm unsat. <0.1 ppm $SO_4$ |
| 3 | +Toca Crude 18 ppm unsat. 1800 gms | 160 | 96% $H_2SO_4$ | <1 ppm unsat. <0.1 ppm $SO_4$ | <1 ppm unsat. <0.1 ppm $SO_4$ |
| 4 | +Toca - Off Sieves++ 100 gal/min. 22 ppm unsat. 900 gms | 170 | 95% $H_2SO_4$ | <1 ppm unsat. <0.1 ppm $SO_4$ 800 gms | <1 ppm unsat. <0.1 ppm $SO_4$ 100 gms |

*Minimum detectable limits <1.0 ppm unsaturates, <0.1 ppm $SO_4$ ion.
+Toca = A crude butane sample obtained from Union Texas Petroleum, division of Allied Chemical Corporation.
++Linde 13x molecular sieves were used.

In the following examples, otherwise performed identically to Examples 2-4, the sulfuric acid column was followed by an activated alumina column and samples of propane, n-butane and isobutane were passed through both columns. The "crude" columns report the levels of unsaturates prior to treatment; the "pure" columns report the levels of unsaturates after treatment.

TABLE 2

| Ex. | Sample | i-butylene (PPM) | 1-butene (PPM) | cis-butene | trans-butene | propylene |
|---|---|---|---|---|---|---|
| 5 | porpane-crude | 2 | 4 | | | 12 |
|   | -pure | ND | ND | | | ND |
| 6 | n-butane-crude | ND | | 14 | 10 | |
|   | -pure | ND | | ND | ND | |
| 7 | i-butane-crude | 26 | 3 | | | |
|   | -pure | ND | .7 | | | |

(ND - None Detected)

All analyses were carried out on a PE900 flame ionization gas chromatograph.

The isobutane column for Example 7 was phenylisocyanate/Poncil C, while the n-butane and propane for Examples 5 and 6 were analyzed on Ag-NO$_3$/ethylene glycol/Chromosorb P as described in Example 1. No sulphate was detected.

EXAMPLES 8-13

Evaluating Hydrocarbons as Propellants

The saturated hydrocarbons, and particularly isobutane, obtained by the present process have been compared to commercial samples of "technical grade" isobutane and "aerosol grade" isobutane. In the examples that follow, levels of unsaturates were determined by the first detection technique of Example 1, and the corrosion was scored according to the following procedure.

Six ounce, unlined aerosol containers were used, each with a Precision, Regular valve and a 0.018 inch stem and a 0.080 inch body, but no dip tube. The cans were filled with 80 mls. of distilled, deionized water, monitoring the water input by volume. They were then cooled in a dry ice, GENETRON® 11 fluorocarbon (CCl$_3$F) slush and 20 mls. of test isobutane distilled in. Finally, air was allowed to enter until the can pressure reached 510 millimeters of mercury. The can was then removed and allowed to attain room temperature. Some cans were exposed in an oven to 110° F., or some other test temperature, for 3 to 6 weeks. For standard comparison, various blank cans were used including one containing water-air and one left empty.

After the indicated test period, the cans were opened, the odor of their contents kept and their corrosions scored according to the following procedure:

AEROSOL CAN CORROSION TESTS SCORING METHOD

The corrosion observed in the cans may be described as follows:

(a) Side Seam Corrosion — corrosion resulting from direct attack on solder seam of cans. When this occurs a white deposit is obtained on the seam in the liquid phase together with a darkening of solder seam in vapor phase.

(b) Interface Corrosion — corrosion or detinning occurring at the interface surfaces which are present when the dome is crimped to the can or where the valve is crimped to dome.

(c) Dome Surfaces — corrosion, detinning or pitting of the curved surfaces comprising the dome itself.

(d) Can Surfaces — corrosion, detinning or pitting on the can surfaces or on the bottom plate.

Results of the corrosion test are reported using the following relative number system:

0 — no corrosion observed
1 — slight detinning
2 — almost complete detinning
3 — completely detinned pit formed with obvious rust formation
4 — heavy pitting For side seam corrosion these numbers designate the general levels of increasing corrosion.

Averaging Method Used — Take the arithmetic mean for each site, a, b, c or d, averaging for each observer. For a general figure of merit, take an average for all four sites. Water in contact with the can surface corrodes much more than does gas against the same surface. Here, score site d, the can surface, for water and for gas. Average each separately with the other sites. One can take a mean of water and gas corrosion indices if desired.

Twenty-two cans, including two standards were evaluated by this technique using, (8) purified crude isobutane containing less than 1 part per million unsaturates, (9) purified isobutane combined with untreated isobutane having a total unsaturate concentration of 3.7 parts per million, (10) purified isobutane and 1 butane at levels of 4.6 parts per million, (11) "aerosol grade" isobutane obtained from the Phillips Company (sold as Hydrocarbon Propellant A-31 ®), (12) unpurified isobutane containing 18 parts per million unsaturates. In addition, (13) a water-air and (14) a blank can were similarly tested and scored. Only the cans of Example 12 produced a bad odor. The results are shown in Tables 3 and 4.

TABLE 1

AEROSOL CAN CORROSION SCORING RESULTS
T = 43° C., 110° F, Time = 35 days

| Ex. | Can No. Scoring* | Side Seam | Interface | Dome Surface | Can Surface Gas | Can Surface Gas |
|---|---|---|---|---|---|---|
| 8 | 1 A | 2.5 | 2.50 | 3.00 | 1.00 | 1.00 |
|   | 2 A | 2.5 | 1.75 | 3.00 | 0.00 | 2.00 |
|   | 3 A | 1.6 | 2.00 | 3.00 | 0.00 | 2.00 |
|   | 4 A | 2.6 | 2.50 | 2.75 | 0.00 | 1.25 |
|   | Mean/ Column | 2.30 | 2.19 | 2.94 | 0.25 | 1.56 |
| 9 | 5 B | 1.75 | 2.50 | 3.00 | 0.00 | 2.50 |
|   | 6 B | 3.00 | 2.50 | 2.25 | 0.50 | 2.35 |
|   | 7 A | 1.75 | 3.00 | 2.25 | 0.50 | 1.00 |
|   | 8 B | 2.25 | 2.25 | 2.75 | 1.25 | 1.50 |
|   | Mean/ Column | 2.19 | 2.56 | 2.56 | 0.56 | 1.34 |
| 10 | 9 C | 2.00 | 3.00 | 2.00 | 0.50 | 0.75 |
|   | 10 A | 1.75 | 2.00 | 2.00 | 0.50 | 2.75 |
|   | 11 C | 2.25 | 2.75 | 2.50 | 0.00 | 1.25 |
|   | 12 A | 1.25 | 2.25 | 2.75 | 0.25 | 0.75 |
|   | Mean/ Column | 1.81 | 2.50 | 2.31 | 0.31 | 1.38 |
| 11 | 13 C | 3 | 3 | 2.75 | 1.50 | 1.50 |
|   | 14 C | 3 | 3 | 2.75 | 1.00 | 2.75 |
|   | 15 B | 2.75 | 3 | 3.00 | 1.00 | 3.00 |
|   | 16 B | 2.75 | 3 | 2.75 | 0.55 | 2.25 |
|   | Mean/ Column | 2.88 | 3.00 | 2.81 | 1.00 | 2.36 |
| 12 | 17 C | 3.50 | 3.25 | 3.25 | 1.75 | 3.00 |
|   | 18 C | 3.50 | 3.50 | 3.00 | 1.50 | 2.50 |
|   | 19 C | 3.75 | 3.50 | 2.50 | 1.00 | 2.00 |
|   | 20 C | 1.35 | 3.00 | 3.00 | 0.75 | 1.75 |
|   | Mean/ Column | 3.03 | 3.31 | 2.94 | 1.25 | 2.31 |
| 13 | 21 C | 3.5 | 4.00 | 3.50 | | 2.75 |
| 14 | 22 C | 4.0 | 3.50 | 3.25 | | 3.75 |

TABLE 1-continued

AEROSOL CAN CORROSION SCORING RESULTS
T = 43° C., 110° F, Time = 35 days

| Ex. | Can No. Scoring* | Side Seam | In-ter-face | Dome Sur-face | Can Sur-face Gas | Can Sur-face Gas |
|---|---|---|---|---|---|---|
| | Mean/ Column | 3.75 | 3.75 | 3.35 | | 3.25 |

*Can Scoring
A Least corrosion, best containers
B Moderate corrosion, but acceptable
C More corroded than A or B, not acceptable These results have been averaged as follows:

TABLE 4

AEROSOL CAN TEST AVERAGE RESULTS
35 days at 43° C.

| Example | Material | Site A Side Seam | B Inter-face | C Domes | D Gas | D $H_2O$ | Means Gas | $H_2O$ | Average |
|---|---|---|---|---|---|---|---|---|---|
| 8 | Purified (2) Toca Crude <1 ppm unsat. | 2.30 | 2.19 | 2.94 | 0.25 | 1.56 | 1.92 | 2.25 | 2.09 |
| 9 | Purified (2) Toca Crude & Untreated Toca 3.7 ppm unsat. | 2.19 | 2.56 | 2.56 | 0.56 | 1.34 | 1.97 | 2.16 | 2.07 |
| 10 | Purified (2) Toca & Butene-1 4.6 ppm unsat. | 1.81 | 2.50 | 2.31 | 0.31 | 1.38 | 1.73 | 2.00 | 1.87 |
| 11 | Phillips Aerosol Grade <1 ppm unsat. | 2.88 | 3.00 | 2.81 | 1.00 | 2.36 | 2.42 | 2.76 | 2.59 |
| 12 | Toca Crude Unpurified 18 ppm unsat. | 3.03 | 3.31 | 2.94 | 1.25 | 2.31 | 2.63 | 2.90 | 2.77 |
| 13 | $H_2O$ Blank | 3.75 | 3.75 | 3.35 | — | 3.25 | — | 3.53 | — |

The conclusion from these tests is that "technical grade" isobutane purified by the present process appears equivalent to or better than the "aerosol grade" isobutane available from the Phillips Company. Note particularly the "scoring" column in Table 3 and the unacceptably high values in both Tables for Example 12. A level of unsaturates below about 4 or 5 parts per million does not appear to materially effect the corrosion. Nevertheless, levels below about 2 or even about 1 part per million are obtainable according to the present process.

EXAMPLE 14

In another test, purified isobutane according to the present process was found to generate somewhat less odors than the Philips' product, which in turn was superior to a faint oil-type odor in an Aeropress product sample analysed to have 11% unsaturates. Both "aerosol grade" products and the purified hydrocarbon were superior to crude isobutane which produced an objectionable odor.

Since it has been found that low levels of unsaturated contaminants in "technical grade" hydrocarbons, and particularly isobutane, render these sources unsatisfactory for use as an aerosol propellant, a technique was developed to remove these low levels of unsaturates to below about 5, and preferably below about 2, and most preferably below abou 1 part per million. Easy and large scale purification of such saturates containing unsaturated contaminants has been successfully demonstrated using a sulfuric acid column, a demister column, and, when necessary, a drying column.

I claim:

1. A method of producing a saturated hydrocarbon selected from the group consisting of n-butane, isobutane and propane with less than about 5 parts per million of unsaturated contaminants comprising the steps:
   (a) passing a saturated hydrocarbon containing more than about 5 parts per million of unsaturated contaminants through a sulfuric acid scrubber for a length of time sufficient to remove unsaturated contaminants in excess of 5 parts per million, and
   (b) passing the outflow from the sulfuric scrubber through a basic demister to remove sulfuric acid mist from the saturated hydrocarbon.

2. A method as claimed in claim 1 wherein said saturated hydrocarbon is isobutane.

3. A method as claimed in claim 1 wherein said sulfuric acid scrubber is operated at a temperature and pressure whereat the unsaturated hydrocarbon is liquid, therby using liquid-liquid contact.

4. A method as claimed in claim 3 wherein said saturated hydrocarbon contacts the sulfuric acid scrubber and liquid around glass rings in a column.

5. A method as claimed in claim 1 wherein the sulfuric acid scrubber is between about 90 and about 100 percent sulfuric acid.

6. A method as claimed in claim 5 wherein the sulfuric acid scrubber contains about 96 percent sulfuric acid.

7. A method as claimed in claim 1 wherein the sulfuric acid scrubber is between about 80 and about 99 percent sulfuric acid and between about 1 and about 20 percent $P_2O_5$.

8. A method as claimed in claim 7 wherein the sulfuric acid scrubber contains about 85 to 90 percent sulfuric acid and about 10 to 15 percent $P_2O_5$.

9. A method as claimed in claim 1 wherein the sulfuric acid scrubber contains a catalyst selected from the group consisting of $CuSO_4$ and $HgSO_4$.

10. A method as claimed in claim 1 wherein the basic demister includes a basic reagent selected from the group consisting of alkali and alkali earth hydroxides, basic oxides and the basic salts.

11. A method as claimed in claim 10 wherein the basic reagent is an alkali earth hydroxide dissolved in water.

12. A method as claimed in claim 11 wherein the basic reagent is from about 5 percent sodium hydroxide to saturated sodium hydroxide.

13. A method as claimed in claim 11 further comprising the step of passing the outflow from the basic scrubber through a drying agent.

14. A method as claimed in claim 10 wherein the basic reagent is alumina.

15. A method as claimed in claim 1 wherein the sulfuric scrubber is a first column maintained at a temperature below the boiling point of the saturated hydrocarbon at the operating pressure, and the basic demister is a second column containing a basic aqueous solution and the method includes passing the saturated hydrocarbon containing more than 5 parts per million unsaturated contaminants through, successively, the first column in a liquid state, the second column in a gaseous state and over a dehydrating agent in a gaseous state.

16. A method as claimed in claim 1 wherein the saturate hydrocarbon containing more than 5 parts per million of unsaturated contaminants is passed through the sulfuric acid scrubber under conditions sufficient to remove unsaturate contaminants in excess of about 2 parts per million.

17. A method as claimed in claim 1 wherein the saturated hydrocarbon containing more than 5 parts per million of unsaturated contaminants is passed through a sulfuric acid scrubber under conditions sufficient to remove unsaturated contaminants in excess of about 1 part per million.

18. A method as claimed in claim 1 further comprising the step of periodically heating the sulfuric acid scrubber reagent to vaporize trapped unsaturated contaminants and regenerate the sulfuric acid scrubber.

* * * * *

UNITED STATES PATENT OFFICE
CERTIFICATE OF CORRECTION

Patent No. 4,108,916  Dated August 22, 1978

Inventor(s) Whitney Harris Mears

It is certified that error appears in the above-identified patent and that said Letters Patent are hereby corrected as shown below:

Col. 1, line 9, ". . . + . . ." should read --combination--

21, "unsatifactory" should read --unsatisfactory--

53, "the demister" should read --the basic demister--

Table 1 - Example 2, "15% $P_2O_4$" should read --15% $P_2O_5$--

Col. 8, line 37, "therby" should read --thereby--

Col. 9, line 4, "ric scrubber" should read --ric acid scrubber--

14, "rate" should read --rated--

Signed and Sealed this

Twelfth Day of June 1979

[SEAL]

Attest:

RUTH C. MASON
Attesting Officer

DONALD W. BANNER
Commissioner of Patents and Trademarks